(12) United States Patent
Zoricak et al.

(10) Patent No.: US 9,688,588 B2
(45) Date of Patent: Jun. 27, 2017

(54) CONTINUOUS ETHYLENE TETRAMERIZATION PROCESS

(71) Applicant: NOVA Chemicals (International) S.A., Fribourg (CH)

(72) Inventors: Peter Zoricak, Calgary (CA); Stephen John Brown, Calgary (CA); P Scott Chisholm, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

(21) Appl. No.: 14/443,838

(22) PCT Filed: Dec. 4, 2013

(86) PCT No.: PCT/CA2013/001003
§ 371 (c)(1),
(2) Date: May 19, 2015

(87) PCT Pub. No.: WO2014/094114
PCT Pub. Date: Jun. 26, 2014

(65) Prior Publication Data
US 2015/0284303 A1 Oct. 8, 2015

(30) Foreign Application Priority Data

Dec. 21, 2012 (CA) ..................... 2800268

(51) Int. Cl.
*C08L 23/00* (2006.01)
*C07C 2/34* (2006.01)
*C07C 2/36* (2006.01)

(52) U.S. Cl.
CPC .................. *C07C 2/34* (2013.01); *C07C 2/36* (2013.01); *C07C 2523/26* (2013.01); *C07C 2531/14* (2013.01); *C07C 2531/22* (2013.01); *C07C 2531/24* (2013.01); *Y02P 20/52* (2015.11)

(58) Field of Classification Search
CPC .. C07C 2/36; C07C 2/34; C07C 11/02; C07C 2531/14; C07C 2531/24; C07C 2531/22; C07C 2523/26
See application file for complete search history.

(56) References Cited

U.S. PATENT DOCUMENTS

| 5,198,563 | A | 3/1993 | Reagen et al. | |
| 7,786,336 | B2 | 8/2010 | Zhang et al. | |
| 8,252,956 | B2 | 8/2012 | Gao et al. | |
| 2006/0173226 | A1 | 8/2006 | Blann et al. | |
| 2006/0229480 | A1 | 10/2006 | Blann et al. | |
| 2010/0222622 | A1* | 9/2010 | Overett et al. | C07C 2/32 585/523 |
| 2014/0142360 | A1* | 5/2014 | Brown et al. | C07C 2/36 585/512 |
| 2016/0237000 | A1* | 8/2016 | Jaber et al. | C07C 2/36 |
| 2016/0303551 | A1* | 10/2016 | Zoricak et al. | B01J 31/143 |

FOREIGN PATENT DOCUMENTS

| CA | 2708011 A1 | 12/2011 |
| WO | 0204119 A1 | 1/2002 |
| WO | 2004056478 A1 | 7/2004 |
| WO | 2004056479 A1 | 7/2004 |

OTHER PUBLICATIONS

Carter, Anthea; Cohen, Steven A.; Cooley, Neil A.; Murphy, Aden; Scutt, James and Wass, Duncan F.; High activity ethylene trimerisation catalysts based on diphosphine ligands; Chemical Commununications, 2002, pp. 858-859.

* cited by examiner

*Primary Examiner* — Nathan M Nutter
(74) *Attorney, Agent, or Firm* — Julie L. Heinrich

(57) ABSTRACT

A continuous flow process for the oligomerization of ethylene using a chromium catalyst having a phosphorus-nitrogen-phosphorus ("P—N—P") ligand provides high selectivity to the desired tetramer (1-octene) with reduced production of coproduct $C_{10}^+$ oligomers. Prior art processes that maximize catalyst activity have provided comparatively poor product selectivity. In particular, the production of larger amounts of $C_{10}^+$ oligomers have been observed under conditions that maximize activity. The present process resolves this problem through the use of a combination of low catalyst concentration and by limiting the octene concentration in the reactor.

9 Claims, 1 Drawing Sheet

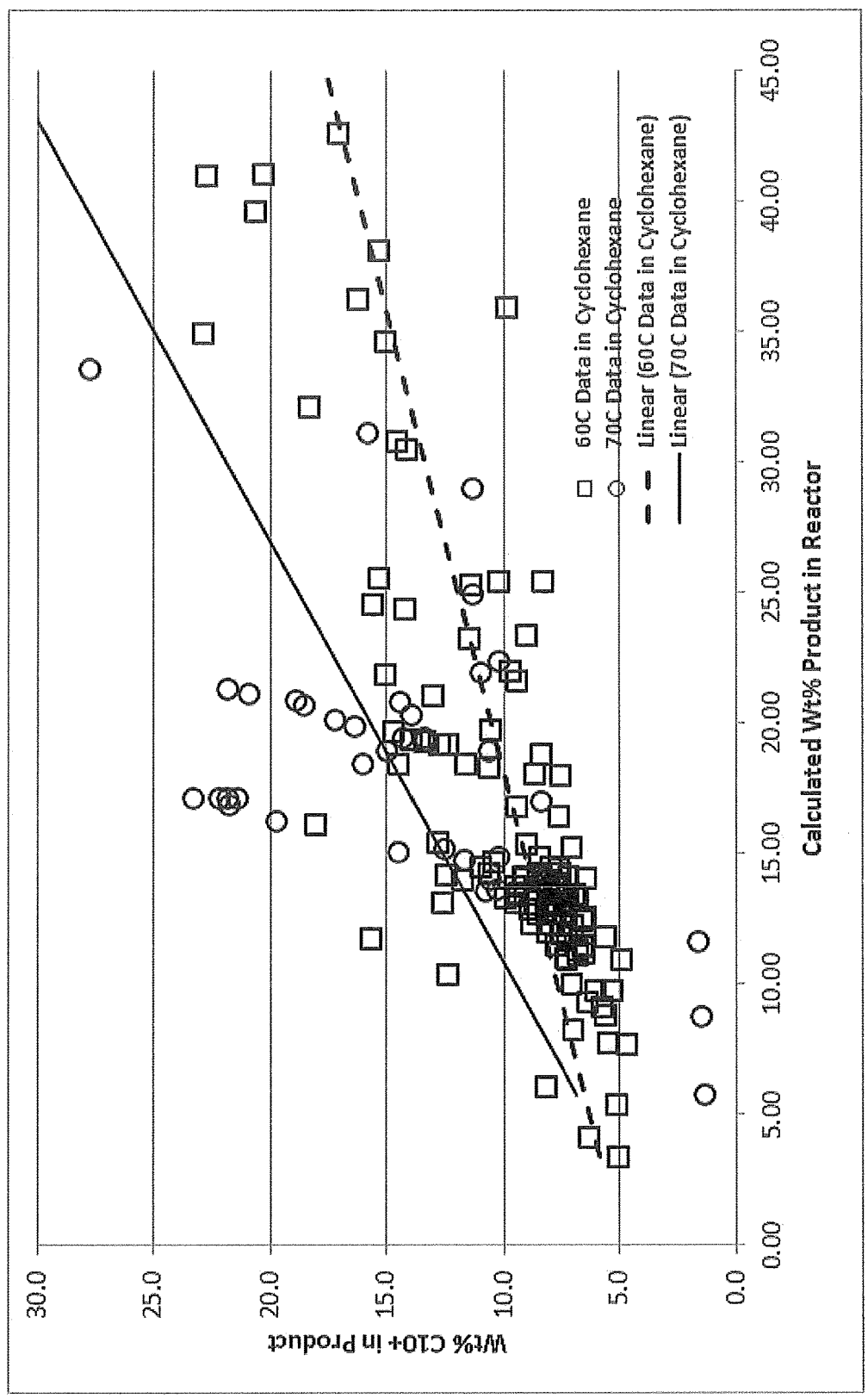

CONTINUOUS ETHYLENE TETRAMERIZATION PROCESS

TECHNICAL FIELD

This invention relates to a continuous flow process for tetramerization of ethylene using a Cr catalyst having a bridged diphosphine ligand.

BACKGROUND ART

Alpha olefins are commercially produced by the oligomerization of ethylene in the presence of a simple alkyl aluminum catalyst (in the so called "chain growth" process) or alternatively, in the presence of an organometallic nickel catalyst (in the so called Shell Higher Olefins, or "SHOP" process). Both of these processes typically produce a crude oligomer product having a broad distribution of alpha olefins with an even number of carbon atoms (i.e. butene-1, hexene-1, octene-1 etc.). The various alpha olefins in the crude oligomer product are then typically separated in a series of distillation columns. Butene-1 is generally the least valuable of these olefins as it is also produced in large quantities as a by-product in various cracking and refining processes. Hexene-1 and octene-1 often command comparatively high prices because these olefins are in high demand as comonomers for linear low density polyethylene (LLDPE).

Technology for the selective trimerization of ethylene to hexene-1 has been recently put into commercial use in response to the demand for hexene-1. The patent literature discloses catalysts which comprise a chromium source and a pyrrolide ligand as being useful for this process—see, for example, ("USP") U.S. Pat. No. 5,198,563 (Reagen et al., assigned to Phillips Petroleum).

Another family of highly active trimerization catalysts is disclosed by Wass et al. in WO 02/04119 (now U.S. Pat. Nos. 7,143,633 and 6,800,702). The catalysts disclosed by Wass et al. are formed from a chromium source and a bridged diphosphine ligand and are described in further detail by Carter et al. (Chem. Comm. 2002, p 858-9). The two phosphorous (P) atoms are preferably bridged by an amine (N) bridge and hence these ligands are typically referred to as "P—N—P" ligands. As described in the Chem. Comm. paper, the most preferred P—N—P ligands are those in which each P atom is bonded to two phenyl groups and each phenyl group is substituted with an ortho-methoxy group. Hexene-1 is produced with high activity and high selectivity by these catalysts.

Similar P—N—P ligands are disclosed by Blann et al. in WO04/056478 and WO 04/056479 (now US 2006/0229480 and US 2006/0173226). However, in comparison to the ligands of Wass et al., the disphosphine/tetraphenyl ligands disclosed by Blann et al. generally do not contain polar substituents in ortho positions. The "tetraphenyl" diphosphine ligands claimed in the '480 application must not have Ortho substituents (of any kind) on all four of the phenyl groups and the "tetraphenyl" diphosphine ligands claimed in '226 are characterized by having a polar substituent in a meta or para position. Both of these types of catalysts reduce the amount of hexenes produced and increase the amount of octene (in comparison to the ligands of Wass et al.) and the catalysts are generally referred to as "tetramerization catalysts".

The performance of Cr bridged diphosphine catalysts is typically temperature dependent. The prior art generally teaches preferred operating temperatures of from 50 to 150° C., especially from 60 to 90° C. Very high activities (of greater than $2\times10^6$ grams of product per gram of catalyst per hour) have been reported at this temperature range, particularly when cyclohexane is used as the solvent. However, simple batch experiments have shown that this high activity is also associated with a decrease in product selectivity—in particular, the production of a higher amount of $C_{10}^+$ oligomers has been observed. These $C_{10}^+$ oligomers have comparatively low value so it is desirable to limit the amount of them that is produced.

Batch experiments have shown that product selectivity may be improved by lowering the reaction temperature (albeit, with a lower catalyst activity also being observed).

However, experiments conducted by us under continuous flow conditions showed that a lower oligomerization temperature is not "sufficient" to minimize the $C_{10}^+$ fraction. Instead, a wide range of product selectivity was observed under continuous flow conditions at a given temperature.

We have now discovered that product selectivity can be improved in a continuous process using quite different conditions. More specifically, selectivity can be increased by using a low chromium concentration and by maintaining low octene concentrations in the reactor. Further improvements may be achieved using lower oligomerization temperatures, so low temperatures are preferred (even though a low temperature is not "sufficient" for a continuous process).

DISCLOSURE OF INVENTION

In one embodiment, the present invention provides:
A continuous flow process for the oligomerization of ethylene, said process comprising
I) adding ethylene and solvent to a mixed reactor and contacting said ethylene under oligomerization conditions with
  1) a diphosphine catalyst defined by the formula $(R^1)(R^2)$—$P^1$-bridge-$P^2(R^3)(R^4)$ wherein $R^1$, $R^2$, $R^3$ and $R^4$ are independently selected from the group consisting of hydrocarbyl and heterohydrocarbyl and the bridge is a moiety that is bonded to both phosphorus atoms;
  2) a source of Cr; and
  3) an activator;
II) removing a product discharge stream comprising hexene, octene, $C_{10}^+$ oligomers and solvent from said reactor; and
III) controlling the flow of said solvent to said reactor such that the product discharge stream contains from 2 to 25 weight % octene, based on the weight of hexene, octene, $C_{10}^+$ oligomers and solvent;
  and wherein said process is further characterized by being conducted at a catalyst concentration of from 0.3 to 5 micromolar Cr;

As noted above, the process of this invention requires that octene concentration in the reactor is controlled/limited. In a continuous flow process, the concentration of octene in the reactor can be controlled by adjusting the solvent flow rate and the rate of reaction. For example, increasing the solvent flow will dilute the octene concentration and decreasing the catalyst concentration will decrease the rate of reaction. Low catalyst concentrations (less than $5\times10^{-6}$ moles of Cr per litre) are required in this process and low temperatures are preferred.

Thus, the process of this invention provides enhanced product through the use of low catalyst concentration and low octene concentrations.

BEST MODE FOR CARRYING OUT THE INVENTION

Part A Catalyst System

The preferred catalyst system used in the process of the present invention must contain three essential components, namely:

(i) a source of chromium;
(ii) a diphosphine ligand; and
(iii) an activator.

Preferred forms of each of these components are discussed below.

Chromium Source ("Component (i)")

Any source of chromium that is soluble in the process solvent and which allows the oligomerization process of the present invention to proceed may be used. Preferred chromium sources include chromium trichloride; chromium (III) 2-ethylhexanoate; chromium (III) acetylacetonate and chromium carbonyl complexes such as chromium hexacarbonyl. It is preferred to use very high purity chromium compounds as these should generally be expected to minimize undesirable side reactions. For example, chromium acetylacetonate having a purity of higher than 99% is commercially available (or may be readily produced from 97% purity material—using recrystallization techniques that are well known to those skilled in the art).

Ligand Used in the Oligomerization Process ("Component (ii)")

In general, the ligand used in the process of this invention is defined by the formula $(R^1)(R^2)$—$P^1$-bridge-$P^2(R^3)(R^4)$ wherein $R^1$, $R^2$, $R^3$ and $R^4$ are independently selected from the group consisting of hydrocarbyl and heterohydrocarbyl and the bridge is a moiety that is bonded to both phosphorus atoms.

The term hydrocarbyl as used herein is intended to convey its conventional meaning—i.e. a moiety that contains only carbon and hydrogen atoms. The hydrocarbyl moiety may be a straight chain; it may be branched (and it will be recognized by those skilled in the art that branched groups are sometimes referred to as "substituted"); it may be saturated or contain unsaturation and it may be cyclic. Preferred hydrocarbyl groups contain from 1 to 20 carbon atoms. Aromatic groups—especially phenyl groups—are especially preferred. The phenyl may be unsubstituted (i.e. a simple $C_6H_5$ moiety) or contain substituents, particularly at an ortho (or "o") position.

Similarly, the term heterohydrocarbyl as used herein is intended to convey its conventional meaning—more particularly, a moiety that contains carbon, hydrogen and at least one heteroatom (such as O, N, R and S). The heterohydrocarbyl groups may be straight chain, branched or cyclic structures. They may be saturated or contain unsaturation. Preferred heterohydrocarbyl groups contain a total of from 2 to 20 carbon+heteroatoms (for clarity, a hypothetical group that contains 2 carbon atoms and one nitrogen atom has a total of 3 carbon+heteroatoms).

It is preferred that each of $R^1$, $R^2$, $R^3$ and $R^4$ is a phenyl group (with an optional substituent in an ortho position on one or more of the phenyl groups).

Highly preferred ligands are those in which $R^1$ to $R^4$ are independently selected from the group consisting of phenyl and o-fluorophenyl. The resulting ligands are useful for the selective tetramerization of ethylene to octene-1 with some co product hexene also being produced.

The term "bridge" as used herein with respect to the ligand refers to a moiety that is bonded to both of the phosphorus atoms in the ligand—in other words, the "bridge" forms a link between $P^1$ and $P^2$. Suitable groups for the bridge include hydrocarbyl and an inorganic moiety selected from the group consisting of $N(CH_3)$—$N(CH_3)$—, —$B(R^6)$—, —$Si(R^6)_2$—, —$P(R^6)$— or —$N(R^6)$— where $R^6$ is selected from the group consisting of hydrogen, hydrocarbyl and halogen.

It is especially preferred that the bridge is —$N(R^5)$— wherein $R^5$ is selected from the group consisting of hydrogen, alkyl, substituted alkyl, aryl, substituted aryl, aryloxy, substituted aryloxy, halogen, alkoxycarbonyl, carbonyloxy, alkoxy, aminocarbonyl, carbonylamino, dialkylamino, silyl groups or derivatives thereof and an aryl group substituted with any of these substituents. Highly preferred bridges are those in which $R^5$ is a $C_1$ to $C_{12}$ alkyl—especially isopropyl (i.e. when $R^5$ is isopropyl).

In one embodiment, two different types of ligands are used to alter the relative amounts of hexene and octene being produced. For clarity: the use of a ligand that produces predominantly hexene may be used in combination with a ligand that produces predominantly octene.

Activator ("Component (iii)")

The activator (component (iii)) may be any compound that generates an active catalyst for ethylene oligomerization with components (i) and (ii). Mixtures of activators may also be used. Suitable compounds include organoaluminum compounds, organoboron compounds and inorganic acids and salts, such as tetrafluoroboric acid etherate, silver tetrafluoroborate, sodium hexafluoroantimonate and the like. Suitable organoaluminium compounds include compounds of the formula $AlR_3$, where each R is independently $C_1$-$C_{12}$ alkyl, oxygen or halide, and compounds such as $LiAlH_4$ and the like. Examples include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and alumoxanes (or aluminoxanes). Alumoxanes are well known in the art as typically oligomeric compounds which can be prepared by the controlled addition of water to an alkylaluminium compound, for example trimethylaluminium. Such compounds can be linear, cyclic, cages or mixtures thereof. Commercially available alumoxanes are generally believed to be mixtures of linear and cyclic compounds. The cyclic alumoxanes can be represented by the formula $[R^6AlO]_s$ and the linear alumoxanes by the formula $R^7(R^8AlO)_s$ wherein s is a number from about 2 to 50, and wherein $R^6$, $R^7$, and $R^8$ represent hydrocarbyl groups, preferably $C_1$ to $C_6$ alkyl groups, for example methyl, ethyl or butyl groups. Alkylalumoxanes especially methylalumoxane (MAO) are preferred.

It will be recognized by those skilled in the art that commercially available alkylalumoxanes may contain a proportion of trialkylaluminium. For instance, some commercial MAO contains approximately 10 wt % trimethylaluminium (TMA), and commercial "modified MAO" (or "MMAO") contains both TMA and TIBA. Quantities of alkylalumoxane are generally quoted herein on a molar basis of aluminium (and include such "free" trialkylaluminium).

The use of additional TEAL is preferred for this invention. The combined use of MAO and TEAL can provide a cost effective cocatalyst system.

In the preparation of the catalyst systems used in the present invention, the quantity of activating compound to be employed is easily determined by simple testing, for example, by the preparation of small test samples which can be used to oligomerize small quantities of ethylene and thus to determine the activity of the produced catalyst. It is generally found that the quantity employed is sufficient to provide 500 to 5000 moles of aluminium per mole of chromium. A mix of MAO and TEAL is the presently preferred activator. Molar Al/Cr ratios of from 1/1 to 1500/1, especially 300/1 to 900/1 are preferred. Additional TEAL increases the total Al/Cr ratio but may actually reduce overall costs as TEAL is much less expensive than MAO. The use of a combined MAO+TEAL cocatalyst system is shown in the examples.

Part B Catalyst: Ratios and Preparation

The chromium (component (i)) and ligand (component (ii)) may be present in any molar ratio which produces oligomer, preferably between 100:1 and 1:100, and most preferably from 10:1 to 1:10, particularly 3:1 to 1:3. Generally the amounts of (i) and (ii) are approximately equal, i.e. a ratio of between 2:1 and 1:2.

Components (i)-(iii) of the catalyst system utilized in the present invention may be added together simultaneously or sequentially, in any order, and in the presence or absence of ethylene in any suitable solvent, so as to give an active catalyst. For example, components (i), (ii) and (iii) and ethylene may be contacted together simultaneously, or components (i), (ii) and (iii) may be added together simultaneously or sequentially in any order and then contacted with ethylene, or components (i) and (ii) may be added together to form an isolable metal-ligand complex and then added to component (iii) and contacted with ethylene, or components (i), (ii) and (iii) may be added together to form an isolable metal-ligand complex and then contacted with ethylene.

For further clarity: the catalyst components may be mixed together in the oligomerization reactor, or—alternatively—some or all of the catalyst components may be mixed together outside of the oligomerization reactor.

A variety of methods are known to purify solvents used to prepare the catalysts including use of molecular sieves (3 A), adsorbent alumina and supported de-oxo copper catalyst. Several configurations for the purifier system are known and depend on the nature of the impurities to be removed, the purification efficiency required and the compatibility of the purifier material and the process solvent. In some configurations, the process solvent is first contacted with molecular sieves, followed by adsorbent alumina, then followed by supported de-oxo copper catalyst and finally followed by molecular sieves. In other configurations, the process solvent is first contacted with molecular sieves, followed by adsorbent alumina and finally followed by molecular sieves. In yet another configuration, the process solvent is contacted with adsorbent alumina. One preferred purifier system consists of molecular sieves, followed by adsorbent alumina and finally followed by another set of molecular sieves.

The catalyst components (i), (ii) and (iii) utilized in the present invention can be unsupported or supported on a support material, for example, silica, alumina, $MgCl_2$ or zirconia, or on a polymer, for example polyethylene, polypropylene, polystyrene, or poly(aminostyrene). If desired the catalysts can be formed in situ in the presence of the support material, or the support material can be pre-impregnated or premixed, simultaneously or sequentially, with one or more of the catalyst components. The quantity of support material employed can vary widely, for example from 100,000 to 1 gram per gram of metal present in the transition metal compound. In some cases, the support material can also act as or as a component of the activator compound (iii). Examples include supports containing alumoxane moieties.

Part C Reaction Conditions (General)

Irrespective of the process conditions employed, the oligomerization is typically carried out under conditions that substantially exclude oxygen, water, and other materials that act as catalyst poisons. In addition, the reactor is preferably purged with a nonreactive gas (such as nitrogen or argon) prior to the introduction of catalyst. A purge with a solution of MAO and/or aluminum alkyl may also be employed to lower the initial level of catalyst poisons. Also, oligomerizations can be carried out in the presence of additives to control selectivity, enhance activity and reduce the amount of polymer formed in oligomerization processes. Potentially suitable additives include, but are not limited to, hydrogen or a halide source (especially the halide sources disclosed in U.S. Pat. No. 7,786,336, Zhang et al.). Other (optional) additives include antistatic agents (such as the polysulfone polymer sold under the trademark Stadis®) and/or fluorocarbons to mitigate reaction fouling. The use of hydrogen is especially preferred because it has been observed to reduce the amount of polymer that is formed.

The process of this invention requires the use of a solvent or diluent.

As shown in the examples, the undesirable formation of $C_{10}{}^+$ oligomers has been observed to increase under continuous flow oligomerization conditions when the concentration of octene in the reactor increases. The addition of a solvent/diluent mitigates this problem. Suitable solvents include saturated $C_6$ to $C_{20}$ aliphatics (such as hexane, heptane, etc.) and saturated cycloaliphatics (such as cyclohexane or methyl cyclohexane). Unsaturated aliphatics (especially 1-olefins such as 1-hexene; 1-heptene and 1-octene) should be avoided.

Mixtures of inert diluents or solvents also could be employed. The preferred solvents are aromatic hydrocarbons or saturated aliphatics such as, for example, isobutane, pentane, toluene, xylene, ethylbenzene, cumene, mesitylene, heptane, cyclohexane, methylcyclohexane, chlorobenzene, dichlorobenzene, and mixtures of aliphatics sold under the trademark Isopar®. Cyclohexane and linear C6 to 010 saturated aliphatics are especially preferred. Heptane is an especially preferred linear aliphatic because it is readily separated from the oligomers produced by this reaction using conventional distillation techniques.

The ethylene feedstock for the oligomerization may be substantially pure or may contain other olefinic impurities and/or ethane.

The feedstock is preferably treated to remove catalyst poisons (such as oxygen, water and polar species) using techniques that are well known to those skilled in the art. The technology used to treat feedstocks for polymerizations is suitable for use in the present invention and includes the molecular sieves, alumina and de-oxo catalysts described above for analogous treatment of the process solvent.

Part D Reactor

The present invention must be conducted under continuous flow conditions using a mixed reactor.

The term "continuous flow" is meant to convey its conventional meaning—i.e. reactants are continuously added to the reactor and product is continuously withdrawn.

Similarly, the term "mixed reactor" is meant to convey its conventional meaning—i.e. a reactor that contains an agitator or mixing system. A continuously stirred tank reactor ("CSTR") is generally preferred. However, a loop reactor in which mixing is provided by a circulating pump is also suitable (and such reactors are well known to those skilled in the art and are in commercial use).

The use of a CSTR is generally preferred as it is desirable to maintain essentially homogenous reactor conditions—i.e. as will be appreciated by those skilled in the art, a well mixed CSTR will provide homogenous reactor conditions (in contrast to a plug flow, or tubular reactor, in which the reactor conditions are typically very different at the inlet and discharge). More than one CSTR may be used.

Although a single CSTR is preferred, it is also within the scope of this invention to (optionally) use an additional tubular reactor. If the tubular reactor is employed, it would be placed downstream of the CSTR. The tubular reactor (if used) would provide some additional ethylene conversion, thereby reducing the need to recover/recycle ethylene from the discharge.

Part E Specific/Preferred Process Conditions

The process of the present invention specifically requires
1) the use of a solvent or diluent; (discussed above)
2) a catalyst concentration of from 0.3 to $5 \times 10^{-6}$ moles of Cr per litre (micromolar).

The reactor temperature is preferably from 30 to 70° C., especially from 35 to 45° C. In general, lower temperatures have been observed to improve selectivity (when other reaction variables are held constant).

Preferred catalyst concentrations are from 0.5 to 3 micromolar. Higher catalyst concentrations generally increase the reaction rate and can reduce product selectivity. Preferred hold up times (HUT) are from 60 to 180 minutes, especially 60 to 90 minutes.

Another preferred element of the present invention is the use of ethylene concentrations of 3 to 15 weight %, especially from 5 to 10 weight %.

The total operating pressure of the process is a function of ethylene concentration, hydrogen concentration (and hydrogen is preferably added to reduce by product polymer formation) and temperature. The use of comparatively low temperature means that a higher ethylene concentration may be achieved at a given pressure (as ethylene solubility increases at lower temperatures). Preferred operating pressures are from 2 to 20 Mega Pascals (MPa) especially from 4 to 10 MPa.

Part F Reactor Control

The control systems required for the operation of agitated reactors are well known to those skilled in the art and do not represent a novel feature of the present invention. In general, temperature, pressure and flow rate readings will provide the basis for most conventional control operations. The increase in process temperature (together with reactor flow rates and the known enthalpy of reaction) may be used to monitor ethylene conversion rates. The amount of catalyst added to the reactor may be increased to increase the ethylene conversion (or conversely, decreased to decrease ethylene conversion) within desired ranges. Thus, basic process control may be derived from simple measurements of temperature, pressure and flow rates using conventional thermocouples, pressure meters and flow meters. Advanced process control (for example, for the purpose of monitoring product selectivity or for the purpose of monitoring process fouling factors) may be undertaken by monitoring additional process parameters with more advanced instrumentation. Known/existing instrumentation that may be employed include in-line/on-line instruments such as NIR infrared, Fourier Transform Infrared (FTIR), Raman, mid-infrared, ultra violet (UV) spectrometry, gas chromatography (GC) analyzer, refractive index, on-line densitometer or viscometer. The use of NIR or GC to measure the composition of the oligomerization reactor and final product composition is especially preferred. A GC analyzer was used to measure the composition of the reactor discharge in the accompanying examples.

The measurement may be used to monitor and control the reaction to achieve the targeted stream properties including but not limited to concentration, viscosity, temperature, pressure, flows, flow ratios, density, chemical composition, phase and phase transition, degree of reaction, polymer content, selectivity.

The control method may include the use of the measurement to calculate a new control set point. The control of the process will include the use of any process control algorithms, which include, but are not limited to the use of PID, neural networks, feedback loop control, forward loop control and adaptive control.

Catalyst Deactivation, Catalyst Removal and Polymer Removal

In general, the oligomerization catalyst is preferably deactivated immediately downstream of the reactor as the product exits the reaction system. This is to prevent polymer formation and potential build up downstream of the reactor and to prevent isomerisation of the 1-olefin product to the undesired internal olefins. It is generally preferred to flash and recover unreacted ethylene before deactivation. However, the option of deactivating the reactor contents prior to flashing and recovering ethylene is also acceptable. The flashing of ethylene is endothermic and may be used as a cooling source.

In general, many polar compounds (such as water, alcohols and carboxylic acids) will deactivate the catalyst. The use of alcohols, amines and/or carboxylic acids is preferred—and combinations of these are contemplated. It is generally found that the quantity employed to deactivate the catalyst is sufficient to provide deactivator to metal (from catalyst+activator) mole ratio between about 0.1 to about 4, especially from 1 to 2 (thus, when MAO is the activator, the deactivator is provided on a ratio based on moles of $Cr^+$ to moles of Al).

The deactivator may be added to the oligomerization product stream before or after the volatile unreacted reagents/diluents and product components are separated. In the event of a runaway reaction (e.g. rapid temperature rise) the deactivator can be immediately fed to the oligomerization reactor to terminate the reaction. The deactivation system may also include a basic compound (such as sodium hydroxide) to minimize isomerization of the products (as activator conditions may facilitate the isomerization of desirable alpha olefins to undesired internal olefins).

Polymer removal (and, optionally, catalyst removal) preferably follows catalyst deactivation. Two "types" of polymer may exist, namely polymer that is dissolved in the process solvent and non-dissolved polymer that is present as a solid or "slurry".

Solid/non-dissolved polymer may be separated using one or more of the following types of equipment: centrifuge; cyclone (or hydrocyclone), a decanter equipped with a skimmer or a filter. Preferred equipment include so called "self-cleaning filters" sold under the name V-auto strainers, self-cleaning screens such as those sold by Johnson Screens Inc. of New Brighton, Minn. and centrifuges such as those sold by Alfa Laval Inc. of Richmond, Va. (including those sold under the trademark Sharples®).

Soluble polymer may be separated from the final product by two distinct operations. Firstly, low molecular weight polymer that remains soluble in the heaviest product fraction ($C_{20+}$) may be left in that fraction. This fraction will be recovered as "bottoms" from the distillation operations (described below). This solution may be used as a fuel for a power generation system.

An alternative polymer separation comprises polymer precipitation caused by the removal of the solvent from the solution, followed by recovery of the precipitated polymer using a conventional extruder. The technology required for such separation/recovery is well known to those skilled in the art of solution polymerization and is widely disclosed in the literature.

In another embodiment, the residual catalyst is treated with an additive that causes some or all of the catalyst to precipitate. The precipitated catalyst is preferably removed from the product at the same time as by-product polymer is removed (and using the same equipment). Many of the catalyst deactivators listed above will also cause catalyst precipitation. In a preferred embodiment, a solid sorbent (such as clay, silica or alumina) is added to the deactivation operation to facilitate removal of the deactivated catalyst by filtration or centrifugation.

Reactor fouling (caused by deposition of polymer and/or catalyst residue) can, if severe enough, cause the process to be shut down for cleaning. The deposits may be removed by known means, especially the use of high pressure water jets or the use of a hot solvent flush. The use of an aromatic solvent (such as chlorobenzene) for solvent flushing is generally preferred because they are good solvents for polyethylene.

Distillation

In one embodiment of the present invention, the oligomerization product produced from this invention is added to a product stream from another alpha olefins manufacturing process for separation into different alpha olefins. As previously discussed, "conventional alpha olefin plants" (wherein the term includes i) those processes which produce alpha olefins by a chain growth process using an aluminum alkyl catalyst, ii) the aforementioned "SHOP" process and iii) the production of olefins from synthesis gas using the so called Lurgi process) have a series of distillation columns to separate the "crude alpha product" (i.e. a mixture of alpha olefins) into alpha olefins (such as butene-1, hexene-1 and octene-1). The mixed hexene-octene product which is preferably produced in accordance with the present invention is highly suitable for addition/mixing with a crude alpha olefin product from an existing alpha olefin plant (or a "cut" or fraction of the product from such a plant) because the mixed hexene-octene product produced in accordance with the present invention can have very low levels of internal olefins. Thus, the hexene-octene product of the present invention can be readily separated in the existing distillation columns of alpha olefin plants (without causing the large burden on the operation of these distillation columns which would otherwise exist if the present hexene-octene product stream contained large quantities of internal olefins). As used herein, the term "liquid product" is meant to refer to the oligomers produced by the process of the present invention which have from 4 to (about) 20 carbon atoms.

In another embodiment, the distillation operation for the oligomerization product is integrated with the distillation system of a solution polymerization plant (as disclosed in Canadian Patent Application No. 2,708,011, Krzywicki et al.).

If toluene is present in the process fluid (for example, as a solvent for a MAO activator), it is preferable to add water to the "liquid product" prior to distillation to form a water/toluene azeotrope with a boiling point between that of hexene and octene.

The process also typically produces hexene as a co-product.

EXAMPLES

The following abbreviations are used in the examples:
C=comparative
GC=gas chromatography
Wt=weight
$C_4$'s=butenes
$C_6$'s=hexenes
$C_8$'s=octenes
C10+=compounds with 10 or more carbons
Oligomerization Reactions Examples Continuous Operation—General Conditions A continuously stirred tank reactor (CSTR) was used for these experiments.

The CSTR reactor was fitted with external jacket for heating/cooling. A feed preparation unit was installed to allow ethylene to be dissolved in solvent prior to being added to the reactor. The feed preparation was also equipped with a cooling jacket (to remove heat of absorption).

The chromium source for the catalyst was chromium tri(acetylacetonate), or $Cr(acac)_3$. The ligand was a P—N—P ligand in which the nitrogen bridging atom was substituted with an isopropyl group and each P atom was substituted with two ortho-fluro phenyl groups. This ligand and its synthesis are known to those skilled in the art. Further details are provided in U.S. Pat. No. 8,252,956 (Gao et al.).

The cocatalyst was a combination of modified MAO (MMAO-3A) and TEAL.

MMAO-3A was purchased as a solution of methylaluminoxine (7 weight % Al in isopentane) from Akzo-Nobel.

TEAL was purchased as a 25 wt % TEAL solution in heptane from Akzo-Nobel. Catalyst, liquid and co-catalyst were added to the reactor (i.e. "in situ" catalyst formation).

The reactor was operated in a continuous manner—i.e. product was removed from the reactor during the reaction and feed (ethylene and solvent and catalyst) was added.

In addition to catalyst and ethylene, hydrogen was also fed to the reactor to reduce the formation of by product polyethylene. Hydrogen is typically fed at between 0.05-0.035 g/min.

Background Examples

Simple (comparative) batch experiments led to the observation that the amount of $C_{10}^+$ oligomer produced during the reaction is generally lower as the oligomerization temperature is decreased. Based on this observation, a series of experiments were conducted under continuous flow conditions at temperatures of 60° C. and 70° C. It was expected that the lower temperature would provide better product selectivity (i.e. more octene and less $C_{10}^+$ oligomers). FIG. 1 illustrates the results from the experiments. The data are widely scattered with little or no obvious effect of temperature on the product distribution.

Two possible reasons for the difference between the batch experiments (which show a temperature effect) and the continuous experiments are that 1) the batch experiments are typically conducted at a comparatively high ethylene concentration (with ethylene being fed upon demand as ethylene is consumed in the reaction) and 2) the batch experiments are typically conducted to a consistent level of ethylene conversion (i.e. the reaction is conducted until a measured amount of ethylene is consumed). In contrast, the ethylene concentration in a CSTR operated in a continuous flow process will be dependent upon a) the rate of ethylene addition; b) the rate of solvent/diluent addition and c) the rate of reaction. Thus, for a given rate of solvent and ethylene addition, a high reaction rate will provide a lower ethylene concentration in the reactor and a higher concentration of the oligomer product in the reactor.

In order to consider these effects, the data in FIG. 1 are provided as a plot of $C_{10}^+$ oligomer formed versus the concentration of product (hexene+octene) in the reactor.

A brief discussion of the data in FIG. 1 follows. The experiments were conducted over a range of ethylene flow rates, solvent (cyclohexene) flow rates and catalyst/co-catalyst flow rates.

The flow rates of the inputs affects the hold up time ("HUT") in a continuous flow reactor, as will be appreciated by those skilled in the art.

In addition, the rate of reaction affects the reactor contents in the following general manner:

For a given ethylene and solvent flow rate, an increase in the reaction rate will increase the amount of oligomer in the reactor and decrease the ethylene concentration. The oligomer contained in the reactor contains the desired octene and hexene (collectively the octene and hexene are referred to in FIG. 1 as "product") and the undesired $C_{10}^+$ coproduct.

As shown in FIG. 1, the amount of $C_{10}^+$ was observed to increase as the amount of product in the discharge stream increased.

For a well mixed CSTR, the composition at the reactor discharge may be regarded as being essentially equivalent to the composition within the reactor (as opposed to a tubular reactor, in which the composition at the discharge of the reactor is generally different from the composition at the start of the tubular reactor). The reactor discharge was analyzed using gas chromatography (GC) to determine the amount of product and $C_{10}^+$ oligomer in the discharge.

Thus, the amount of octene that is measured in the product discharge stream may be considered to be a very good indicator of the amount of octene contained in the reactor.

Accordingly, the data provided in FIG. 1 show that the amount of $C_{10}^+$ oligomer that is produced in a continuous flow CSTR is a function of the amount of "product" in the reactor.

Example 1 Comparative

The data shown in FIG. 1 generally indicate that the amount of $C_{10}^+$ oligomer being produced increases as the concentration of octene (plus hexene) increases in the reactor. While not wishing to be bound by theory, this suggests that the octene that is produced during the reaction may itself become a reactant for a secondary reaction that produces the $C_{10}^+$ oligomer under the continuous flow conditions described above.

Example 2 Comparative

The same liquid, Cr source, MAO and TEAL used in the previous example were used in this example.

Octene was used as the solvent (instead of the cyclohexane used in the above example).

General conditions for the experiments follow:
Ligand/Cr (mole ratio): 1.1 to 1
MAO/Cr (mole ratio): (a.p.) of 600/1
TEAL/Cr (mole ratio): a.p. of 1500:1
Temperatures are as reported in Table 1.
Various Cr concentrations were studied as reported in table 1. The Cr concentration in the reactor is controlled/adjusted by adjusting the flow rates of Cr and/or solvent to the reactor.

The rate of reaction and the rate of solvent flow alter the ethylene concentration in the reactor. Ethylene measured in the reactor discharge (by GC) is assumed to be equivalent to the reactor ethylene concentration. Ethylene concentrations are reported in Table 1.

The hexene ($C_6$); octene ($C_8$) and $C_{10}^+$ fractions in the reactor discharge may be readily determined by GC.

As shown in Table 1, the use of 1-octene as the solvent/diluent produces very high levels of $C_{10}$ oligomers under the continuous flow conditions of this example. Specifically, the amount of $C_{10}$ oligomer produced in these experiments was found to be from about 32 to 58 weight % (based on the amount of ethylene converted).

In general, octene would be (otherwise) considered to be a potentially good solvent for the tetramerization reaction because 1) it is an aliphatic (with fewer health/safety/exposure concerns compared to an aromatic solvent) and because 2) it is the desired "product" from the tetramerization reaction (which means that product work up/separation/purification processes should be simplified). However, the data in Table 1 show that octene is not a suitable solvent for this process. As noted above, the data suggest that octene reacts with the catalyst system to produce $C_{10}^+$ oligomers under the continuous flow conditions of this example.

TABLE 1

| | Comparative | | | | | |
|---|---|---|---|---|---|---|
| Run # | Reactor [Cr] Concentration (µM)* | Reactor [Ethylene] Concentration (wt %) | Reactor HUT (min)* | Reactor temp (° C.) | Productivity (gProduct/gCr) | C-10+ (wt %) |
| 1 | 2.06 | 2.47 | 49.35 | 70 | 1,211,815 | 58.0 |
| 2 | 0.70 | 5.34 | 66.99 | 70 | 4,416,636 | 41.7 |
| 3 | 1.88 | 3.90 | 179.90 | 70 | 5,228,193 | 31.7 |
| 4 | 1.87 | 3.24 | 178.66 | 60 | 5,277,880 | 49.5 |
| 5 | 1.88 | 3.90 | 179.90 | 50 | 5,228,193 | 50.4 |
| 6 | 1.92 | 6.03 | 184.02 | 45 | 5,068,090 | 45.4 |
| 7 | 1.62 | 6.13 | 194.28 | 45 | 6,355,815 | 40.9 |

TABLE 2

| Run # | Reactor [Cr] Concentration micromolar | Reactor [Ethylene] Concentration (wt %) | Reactor HUT (min)* | Reactor Temp. (° C.) | Calculated Wt % Product in Reactor | Productivity (gProduct/gCr) | C6s (wt %)** | C8s (wt %)** | C-10 & C-10+ (wt %) |
|---|---|---|---|---|---|---|---|---|---|
| 1 | 2.06 | 2.02 | 49.20 | 70.0 | 16.89 | 1,232,517 | 59.5 | 18.4 | 21.7 |
| 2 | 1.36 | 23.94 | 130.57 | 45.0 | 15.11 | 2,136,548 | 22.7 | 62.4 | 14.8 |
| 3 | 2.07 | 2.65 | 49.54 | 70.0 | 16.27 | 1,186,971 | 56.7 | 23.3 | 19.7 |
| 4 | 1.11 | 7.93 | 106.21 | 70.0 | 31.13 | 4,400,074 | 49.1 | 34.9 | 15.8 |
| 5 | 1.19 | 13.71 | 113.88 | 60.0 | 25.35 | 3,582,996 | 33.3 | 55.1 | 11.4 |
| 6 | 1.22 | 15.90 | 117.08 | 50.0 | 23.16 | 3,273,831 | 21.8 | 66.2 | 11.8 |
| 7 | 2.05 | 1.76 | 49.05 | 70.0 | 17.16 | 1,251,840 | 60.5 | 17.5 | 21.8 |
| 8 | 2.07 | 2.78 | 49.61 | 60.0 | 16.13 | 1,177,310 | 50.5 | 31.1 | 18.1 |
| 9 | 2.15 | 5.75 | 51.33 | 50.0 | 13.16 | 960,618 | 31.1 | 56.7 | 12.0 |
| 10 | 2.20 | 7.91 | 52.65 | 45.0 | 11.01 | 803,276 | 22.5 | 66.6 | 10.6 |
| 11 | 3.58 | 4.55 | 85.57 | 45.0 | 27.92 | 1,186,971 | 27.1 | 51.8 | 20.6 |
| 12 | 2.97 | 6.03 | 94.72 | 45.0 | 29.43 | 1,527,420 | 25.4 | 54.3 | 19.9 |
| 13 | 2.21 | 7.42 | 105.58 | 45.0 | 31.63 | 2,235,922 | 22.7 | 56.8 | 20.1 |
| 14 | 1.27 | 10.87 | 121.74 | 45.0 | 32.60 | 4,140,596 | 19.3 | 62.7 | 17.7 |
| 15 | 2.10 | 3.20 | 100.66 | 70.0 | 35.85 | 2,534,045 | 57.3 | 24.5 | 18.0 |
| 16 | 2.18 | 6.17 | 104.07 | 45.0 | 32.88 | 2,324,255 | 24.1 | 57.3 | 18.3 |
| 17 | 1.27 | 10.47 | 121.17 | 45.0 | 32.99 | 4,190,283 | 20.4 | 62.1 | 17.2 |
| 18 | 1.19 | 4.91 | 113.62 | 70.0 | 38.55 | 4,896,945 | 53.7 | 33.9 | 12.1 |
| 19 | 1.43 | 20.21 | 137.12 | 45.0 | 23.25 | 2,953,625 | 16.1 | 70.1 | 13.6 |
| 20 | 3.70 | 7.60 | 88.63 | 45.0 | 24.87 | 1,057,232 | 23.4 | 65.3 | 10.7 |
| 21 | 2.19 | 6.95 | 105.01 | 45.0 | 32.10 | 2,269,047 | 24.1 | 56.7 | 18.7 |
| 22 | 2.25 | 9.06 | 107.63 | 45.0 | 29.99 | 2,119,985 | 15.5 | 70.0 | 14.2 |
| 23 | 2.11 | 7.62 | 100.94 | 45.0 | 29.55 | 2,194,516 | 19.1 | 64.0 | 16.6 |
| 24 | 3.67 | 6.82 | 87.83 | 45.0 | 25.65 | 1,090,357 | 22.2 | 62.4 | 15.0 |
| 25 | 1.27 | 10.56 | 121.30 | 45.0 | 32.90 | 4,179,242 | 20.0 | 60.3 | 19.5 |
| 26 | 1.17 | 8.15 | 111.89 | 70.0 | 33.00 | 4,427,678 | 42.1 | 44.5 | 13.2 |
| 27 | 3.72 | 7.95 | 89.00 | 45.0 | 24.51 | 1,042,050 | 20.1 | 65.3 | 14.1 |
| 28 | 2.27 | 9.84 | 108.63 | 45.0 | 29.21 | 2,064,777 | 19.6 | 62.3 | 17.8 |
| 29 | 3.84 | 10.65 | 91.91 | 45.0 | 21.82 | 927,494 | 19.1 | 69.9 | 10.6 |
| 30 | 1.45 | 21.21 | 139.00 | 45.0 | 22.25 | 2,826,647 | 14.0 | 71.3 | 14.6 |
| 31 | 2.05 | 1.80 | 49.07 | 70.0 | 17.12 | 1,249,080 | 60.0 | 16.3 | 23.3 |
| 32 | 0.71 | 6.09 | 67.82 | 70.0 | 18.98 | 4,179,242 | 55.1 | 29.7 | 15.0 |
| 33 | 2.05 | 1.80 | 49.07 | 70.0 | 17.12 | 1,249,080 | 60.9 | 17.5 | 21.4 |
| 34 | 0.71 | 6.59 | 68.22 | 70.0 | 18.48 | 4,068,826 | 55.3 | 28.4 | 16.0 |
| 35 | 0.70 | 4.91 | 66.91 | 70.0 | 20.16 | 4,438,719 | 56.6 | 25.9 | 17.2 |
| 36 | 0.70 | 5.26 | 67.18 | 70.0 | 19.81 | 4,361,428 | 53.1 | 33.4 | 13.2 |
| 37 | 0.70 | 5.01 | 66.99 | 70.0 | 20.06 | 4,416,636 | 52.5 | 34.0 | 13.2 |

Inventive Example

The inventive experiments of this example were conducted in a CSTR using a nominal volume of 2 litres. Cyclohexane was used as the solvent.

The same Cr source (Cr(acac)$_3$); MAO; TEAL and ligand used in the above described examples were used for the experiments of this example.

The ligand/Cr ratio (aiming point) was 1.1/1 for all experiments. The MAO/Cr (molar ratio) aiming point provided an Al/Cr ratio of 600/1. The TEAL/Cr (molar ratio) aiming point provided an Al/Cr ratio of 750/1; thus the total Al/Cr ratio was 1350/1 for these experiments. Hydrogen was also used as described in the prior examples. Total reactor pressure was 8 MPa for these experiments.

The catalyst and co-catalyst components were added to the reactor (i.e. insitu catalyst formation). A wide range of catalyst and solvent flow rates were studied. The reactor discharge was analyzed by GC in order to measure ethylene, hexene, octene and $C_{10}^+$ oligomers.

"Productivity" is calculated by dividing the amount of ethylene that is reacted by the amount of chromium in the reactor. Productivity values are expressed in grams (of ethylene consumed) per gram of chromium. Values are shown in Table 2. The term "product concentration" in Table 2 is calculated by dividing the amount of "product" (i.e. ethylene that is converted in the reactor) by the total reactor contents (product+solvent) and is expressed as weight % in Table 2.

The GC analysis showed that the oligomer product essentially consisted of hexenes ($C_6$ in Table 2), octenes ($C_8$ in Table 2) and $C_{10}^+$ oligomers ($C_{10}^+$ in Table 2)—i.e. little butene was observed.

The values for $C_6$, and $C_{10}^+$ in Table 2 reflect the weight fraction of each component, based on the combined weight of $C_6+C_8+C_{10}^+$.

Reaction temperatures between 45 and 70° C. were studied, as indicated in Table 2. Lower reaction temperatures are preferred. Further experimentation at temperatures as low as 35° C. (not shown) indicate that such temperatures are also suitable.

Table 2 also shows "ethylene concentration" (weight %) as a reaction variable. The ethylene concentration is influenced by the rate of solvent addition and the rate of reaction (for clarity: increasing the reaction rate and the solvent flow rate will decrease the ethylene concentration). As shown in Table 2, a reduction in ethylene concentration (especially to levels of less than 5 weight %) generally increases the amount of hexene that is formed and decreases the amount of octene. It is generally preferred to produce at least 30 weight % octene, so ethylene concentrations of at least 5 weight % are preferred.

The quality of the $C_6$ and $C_8$ streams was also analyzed at various times to determine the amount of alpha olefin (versus internal olefins). The catalyst system used in these examples is highly preferred because it has been observed to produce very high "alpha purity" for both of the hexene and octene streams (in prior "batch" oligomerization reactions).

This behavior was also observed for the continuous reactions. More specifically, the "alpha purity" of the hexene and octene streams was greater than 95% for all of the samples that were analyzed (i.e. less than 5% internal olefins was observed).

Reactor hold up time (HUT) in Table 2 is calculated by dividing the volumetric flow rate (ml/minute) by the reactor volume (ml).

The present invention requires that the amount of octene in the reactor is from 2 to 25 weight % of the reactor contents. For clarity: example 1 of Table 2 shows that the reactor contains 16.89 weight % "product" and that the product is 18.4% octene, which corresponds to 3% octene in the reactor. Similarly, example 2 shows a reactor concentration of 15.11% product (of which 62.4% is octene) for an octene concentration in the reactor of 9.3%.

INDUSTRIAL APPLICABILITY

A new process for the selective oligomerization of ethylene using a catalyst comprising a source of chromium and a P—N—P ligand is provided. The product and by-product distribution can be improved by controlling the chromium concentration. The alpha olefin products that are produced by the invention are suitable for use as comonomers for the preparation of ethylene-alpha olefin copolymers.

The invention claimed is:

1. A continuous flow process for the oligomerization of ethylene, said process comprising
   I) adding ethylene and solvent to a single mixed reactor and contacting said ethylene under continuous flow oligomerization conditions with
      1) a diphosphine catalyst defined by the formula (R1)(R2)-P1-bridge-P2(R3)(R4) wherein R1, R2, R3 and R4 are independently selected from the group consisting of hydrocarbyl and heterohydrocarbyl and the bridge is a moiety that is bonded to both phosphorus atoms;
      2) a source of Cr; and
      3) an activator
   II) removing a product discharge stream comprising hexene, octene, C10+ oligomers and solvent from said reactor; and
   III) controlling the flow of said solvent and ethylene to said reactor such that the product discharge stream contains from 2 to 25 weight % octene, based on the weight of hexene, octene, C10+ oligomers and solvent; and wherein said process is further characterized by i) being conducted at a catalyst concentration of from 0.3 to 5 micromolar Cr and ii) said diphosphine catalyst is prepared and activated in-situ by combining said Cr, said activator, ethylene, and a ligand defined by the formula (R1)(R2)-P1-bridge-P2(R3)(R4) wherein R1, R2, R3 and R4 are independently selected from the group consisting of hydrocarbyl and heterohydrocarbyl and the bridge is a moiety that is bonded to both phosphorus atoms, within said single mixed reactor and wherein said solvent is selected from the group consisting of saturated $C_6$ to $C_{20}$ aliphatics and saturated aliphatics.

2. The process of claim 1 wherein said activator comprises an aluminoxane plus an alkyl aluminum.

3. The process of claim 2 wherein said aluminoxane consists essentially of methylaluminoxane and said alkyl aluminum consists essentially of triethylaluminum (TEA) TEAL.

4. The process of claim 3 wherein the total amount of aluminum contained in said aluminoxane plus said triethylaluminum is sufficient to provide an Al: Cr molar ratio of from 500:1 to 2000:1.

5. The process of claim 1 when conducted at a pressure of from 2 to 20 MPa.

6. The process of claim 1 when conducted at a temperature of from 30 to 70° C.

7. The process of claim 1 wherein said solvent is selected from the group consisting of cyclohexane and heptane.

8. The process of claim 1 wherein the concentration of ethylene in said mixed reactor is from 5 to 20 weight %.

9. The process of claim 1 when conducted at a temperature of from 35 to 45° C., an ethylene concentration of from 5 to 20 weight % and wherein said solvent is selected from the group consisting of cyclohexane and heptane.

* * * * *